US012748093B2

(12) United States Patent
Draskovic et al.

(10) Patent No.: US 12,748,093 B2
(45) Date of Patent: Sep. 29, 2026

(54) FLOW REGIME CLASSIFICATION, WATER LIQUID RATIO ESTIMATION, AND SALINITY ESTIMATION SYSTEMS AND METHODS

(71) Applicant: OenSubsea IP UK Limited, London (GB)

(72) Inventors: Gordana Draskovic, Clamart (FR); Josselin Kherroubi, Clamart (FR); Harald Solheim, Sandsli (NO)

(73) Assignee: OneSubsea IP UK Limited, London (GB)

( * ) Notice: Subject to any disclaimer, the term of this patent is extended or adjusted under 35 U.S.C. 154(b) by 429 days.

(21) Appl. No.: 18/556,757

(22) PCT Filed: Apr. 21, 2022

(86) PCT No.: PCT/US2022/025726

§ 371 (c)(1),
(2) Date: Oct. 23, 2023

(87) PCT Pub. No.: WO2022/226167

PCT Pub. Date: Oct. 27, 2022

(65) Prior Publication Data

US 2024/0192189 A1 Jun. 13, 2024

Related U.S. Application Data

(60) Provisional application No. 63/177,482, filed on Apr. 21, 2021, provisional application No. 63/177,497, filed on Apr. 21, 2021.

(51) Int. Cl.

| | |
|---|---|
| ***G01N 33/18*** | (2006.01) |
| ***G01N 22/04*** | (2006.01) |
| *G01N 33/28* | (2006.01) |

(52) U.S. Cl.

CPC ........... *G01N 33/182* (2013.01); *G01N 22/04* (2013.01); *G01N 33/2847* (2013.01)

(58) Field of Classification Search

CPC ........... G01N 33/2847; G01N 33/2823; G01N 33/241; G01N 33/2835; G01N 22/00; G01N 22/04; E21B 49/08; E21B 49/10

See application file for complete search history.

(56) References Cited

U.S. PATENT DOCUMENTS 4,996,490 A * 2/1991 Scott ...................... G01N 22/00 324/639
11,733,079 B2 * 8/2023 Feng ......................... G01F 1/74 73/152.29

(Continued)

FOREIGN PATENT DOCUMENTS

CN 107748245 A * 3/2018 ............. G06N 3/084
GB 2429067 A * 2/2007 ......... G01N 33/2823

(Continued)

OTHER PUBLICATIONS

Machine translation of CN 107748245 (Year: 2018).*

(Continued)

*Primary Examiner* — Nathaniel J Kolb
(74) *Attorney, Agent, or Firm* — Kyle R. Miiller

(57) ABSTRACT

Water detection and on-line measurement of water salinity is important for many applications in multiphase and wet gas flow metering. A system includes a sensor that measures a microwave signal reflected from a fluid and that generates measurement data based on the reflected microwave signal. The system also includes a processor that performs operations including receiving the measurement data, determining a set of fluid properties based on the measurement data, and receiving fluid classification data associated with the fluid; and generating a water in liquid ratio estimation or salinity (Continued)

value based on an analysis of the measurement data, the fluid classification data, the set of fluid properties, or any combination thereof.

4 Claims, 9 Drawing Sheets

(56) References Cited

U.S. PATENT DOCUMENTS

| | | | | |
|---|---|---|---|---|
| 2006/0145709 | A1 * | 7/2006 | Bentolila | G01N 33/2823 324/717 |
| 2009/0088985 | A1 * | 4/2009 | Wee | G01F 1/712 702/30 |
| 2009/0268203 | A1 | 10/2009 | Uzunbajakava | |
| 2015/0205000 | A1 | 7/2015 | Perkins | |
| 2016/0115395 | A1 * | 4/2016 | Rustad | C10G 33/08 700/282 |
| 2018/0356356 | A1 * | 12/2018 | Black | G06F 15/00 |
| 2018/0371905 | A1 | 12/2018 | Chen | |
| 2020/0041395 | A1 | 2/2020 | Swett | |
| 2021/0372838 | A1 * | 12/2021 | Feng | G01F 1/42 |

FOREIGN PATENT DOCUMENTS

| | | | | | |
|---|---|---|---|---|---|
| NL | 2021236 | B1 | * | 1/2020 | E21B 47/107 |
| WO | 2020009569 | A1 | | 1/2020 | |

OTHER PUBLICATIONS

Machine translation of NL 2021236 (Year: 2021).*

Search Report and Written Opinion of International Patent Application No. PCT/US2022/025726 dated on Aug. 12, 2022, 10 Pages.

Solheim, H. et al., "Artificial intelligence applied to non-intrusive subsea water analysis sensors for enhanced functionality and improved accuracy", MCEDD Deepwater Development, 2021, 21 Pages.

* cited by examiner

FLOW REGIME CLASSIFICATION, WATER LIQUID RATIO ESTIMATION, AND SALINITY ESTIMATION SYSTEMS AND METHODS

CROSS-REFERENCE TO RELATED APPLICATION

This application is a National Stage entry of International Patent Application No. PCT/US2022/025726, filed on Apr. 21, 2022, which claims priority to and the benefit of U.S. Provisional Application No. 63/177,497, entitled "FLOW REGIME CLASSIFICATION METHOD," filed on Apr. 21, 2021, and U.S. Provisional Application No. 63/177,482, entitled "WATER LIQUID RATIO ESTIMATION METHOD," filed on Apr. 21, 2021, both of which are hereby incorporated by reference in their entirety for all purposes.

BACKGROUND

The present disclosure generally relates to systems and methods for flow measurement. In particular, the present disclosure relates to flow regime classifications, water in liquid ratio estimations, and salinity estimations.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it may be understood that these statements are to be read in this light, and not as admissions of prior art.

Water detection and on-line measurement of water salinity is important for many applications in multiphase and wet gas flow metering. Measurement of water quantity and/or quality may assist with detecting formation water breakthrough for reservoir management and flow assurance purposes, as well as to update the water property input to multiphase flow meters. Flow measurement may assist with detecting formation water breakthrough for reservoir management and flow assurance purposes to update the water property input to multiphase flow meters. In the gas and wet gas domains, gas hydrate may form during water production. To remedy gas hydrate formation, the quantity of water may be used to determine adequate pre-emptive chemical dosing prior to water production and increase the chemical dosage when water production is identified. Injected water may be used to increase oil recovery. In the multiphase domain, injected water may have a different salinity than the formation water. As such, monitoring the salinity of the water produced from each well may assist in detection of the produced water. Accordingly, there is a need to monitor the quality and/or the amount of water being produced at a well.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method includes receiving measurement data, the measurement data corresponding to a microwave signal reflected from a fluid, determining a set of fluid properties based on the measurement data, determining a set of fluid classification probabilities based on an analysis of the measurement data, the set of fluid properties, or a combination thereof, and generating a fluid classification associated with the fluid based on the set of fluid classification probabilities. The method also includes transmitting the fluid classification to a control system of an oil and gas extraction system, wherein the control system is configured to adjust operation of one or more components of the oil and gas extraction system based on the fluid classification.

In another embodiment, a system includes a sensor that measures a microwave signal reflected from a fluid and that generates measurement data based on the reflected microwave signal. The system also includes a processor that performs operations including receiving the measurement data, determining a set of fluid properties based on the measurement data, and receiving fluid classification data associated with the fluid; and generating a water in liquid ratio estimation or salinity value based on an analysis of the measurement data, the fluid classification data, the set of fluid properties, or any combination thereof. The operations also include transmitting the water in liquid ratio estimation to a control system of an oil and gas extraction system, wherein the control system is configured to adjust chemical injection in an injection well based on the water in liquid ratio estimation.

In another embodiment, one or more non-transitory, computer-readable media including instructions that, when executed by processing circuitry, are configured to cause the processing circuitry to receive measurement data associated with a fluid, the measurement data corresponding to a microwave signal reflected from the fluid, determine a set of fluid properties based on the measurement data, and receive fluid classification data associated with the fluid, and generate a salinity value associated with the fluid based on an analysis of the measurement data, the set of fluid properties, the fluid classification data, or any combination thereof. The instructions, when executed by the processing circuitry, are also configured to cause the processing circuitry to transmit the salinity value to a control system of an oil and gas extraction system, wherein the control system is configured to adjust operation of one or more components of the oil and gas extraction system based on the salinity value.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
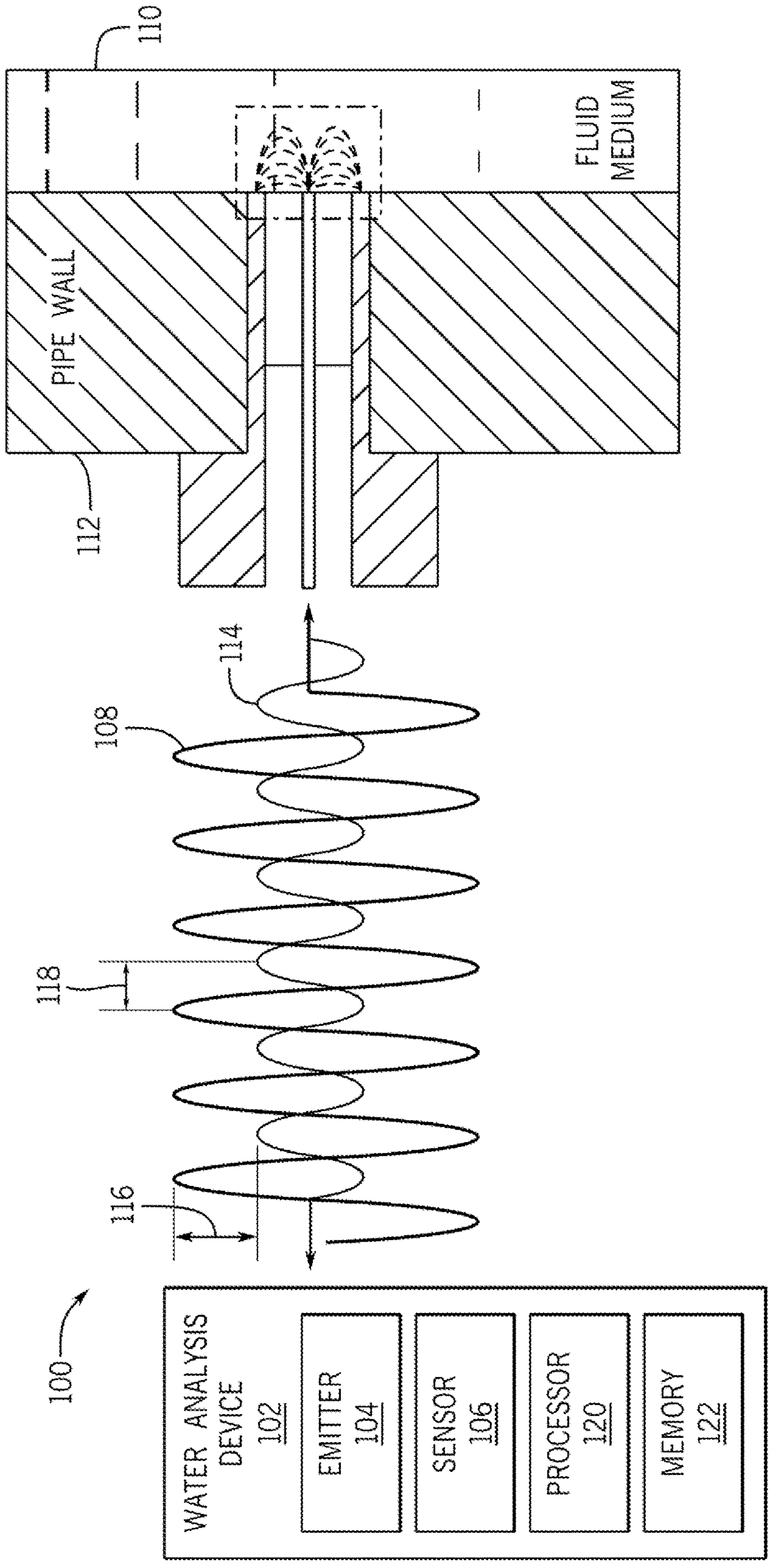
FIG. 1 is a schematic view of a system including a water analysis device, according to an embodiment of the present disclosure.

Certain embodiments commensurate in scope with the present disclosure are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

As used herein, the term "coupled" or "coupled to" may indicate establishing either a direct or indirect connection (e.g., where the connection may not include or include intermediate or intervening components between those coupled), and is not limited to either unless expressly referenced as such. The term "set" may refer to one or more items. Wherever possible, like or identical reference numerals are used in the figures to identify common or the same elements. The figures are not necessarily to scale and certain features and certain views of the figures may be shown exaggerated in scale for purposes of clarification.

Hydrocarbon fluids, such as oil and natural gas, may be obtained from subterranean or subsea geologic formations, often referred to as reservoirs, by drilling one or more wells that penetrate the hydrocarbon-bearing geologic formation. A water analysis device may detect and characterize water in the produced multiphase and/or wet-gas flow that may consist of heterogeneous mixtures of gas, oil, and/or water. The water analysis device (e.g., water analyzer) may detect minute quantities of water. The water analysis device may assist in determining fluid classifications, salinity amounts, and water in liquid ratio amounts.

With the foregoing in mind, FIG. 1 is a schematic view of a system 100 including a water analysis device 102 (e.g., water analyzer or water analysis sensor), according to an embodiment of the present disclosure. The water analysis device 102 is configured to analyze a fluid to determine various parameters (e.g., composition, permittivity, and/or conductivity) of water in a fluid flow, such as multiphase and wet-gas flows. The following discussion refers to a water analysis device 102; however, the device 102 may be generally described as a fluid analysis device, fluid analyzer, or fluid analysis sensor, which may be configured to detect and characterize substances in a fluid flow, such as water, oil, gas, solids, or other substances. The water analysis device 102 may include an emitter 104 and a sensor 106. The emitter 104 may include an open-ended, coaxial probe. The emitter 104 may generate a microwave signal 108 that may reflect in a fluid 110 inside a pipe 112. The sensor 106 may receive a reflected microwave signal 114. The sensor 106 may perform one or more measurements per second (e.g., 100, 500, 1,000, 10,000, and so forth). The water analysis device 102 may determine an attenuation 116 between the microwave signal 108 and the reflected microwave signal 114. Additionally, the water analysis device 102 may determine a phase-shift 118 between the microwave signal 108 and the reflected microwave signal 114. The water analysis device 102 may also include a processor 120 and memory 122. The processor 120 may process measurement data generated by the sensor 106 based on the microwave signals 108, 114. The memory 122 may include any tangible, non-transitory, and computer-readable storage media. The memory 122 may store instructions associated with the functions and processes described herein. Additionally or alternatively, the memory 122 may store measurement data generated by the sensor 106.

The processor 120 may perform instructions stored on the memory 122. In some embodiments, the processor 120 may determine a set of fluid properties associated with the fluid based on the measurement data. For example, the processor 120 may determine permittivity and/or conductivity values associated with the fluid. Additionally or alternatively, the processor 120 may determine values for the set of fluid properties based on a threshold time period. For example, the processor 120 may determine average values, minimum values, maximum values, standard deviation values, or any combination thereof over the threshold time period. The threshold time period may be any time period, such as 5 seconds, 10 seconds, 30 seconds, 1 minute, and so forth. In certain embodiments, the processor 120 may determine additional values for the set of fluid properties. For example, the processor 120 may determine a difference value between the maximum value and the minimum value corresponding to a fluid property. Additionally or alternatively, the processor 120 may determine fluid property value ratios between any two fluid property values. For example, the processor 120 may determine a ratio between a maximum permittivity value and a maximum conductivity value. The processor 120 may also determine a gas volume fraction (GVF). The GVF may be a fraction of the total volumetric flow attributed to gas flow. That is, the GVF is a ratio between the gas volumetric flow rate and the total volumetric flow rate. In some embodiments, the processor 120 may receive the GVF measurements from a flow meter device. Additionally or alternatively, the processor 120 may determine the GVF based on measurement data associated with the fluid, such as hydrocarbon composition, pressure measurements, temperature measurements, and so forth. In certain embodiments, an oil and/or gas well may include a particular GVF measurement as a fixed GVF and the processor 120 may receive the fixed GVF corresponding to the oil and/or gas well. Additionally or alternatively, the processor 120 may receive additional measurement data, such as temperature measurements associated with the fluid, pressure measurements associated with the fluid, and so forth. In some embodiments, the water analysis device 102 may include a receiver and/or a transmitter for receiving and/or transmitting data, signals, and the like. For example, the water analysis device 102 may be communicatively coupled to and/or a component of an oil and/or gas extraction system. In some embodiments, the water analysis device 102 may be a component of an oil and/or gas extraction system and may be communicatively coupled to any number of additional components of the oil and/or gas extraction system. The water analysis device 102 may be communicatively coupled (e.g., wired and/or wireless) to a control system (e.g., any suitable computing device) of an oil and/or gas extraction system. In certain embodiments, the water analysis device 102 may transmit data to the control system, such as a fluid classification, a water in liquid ratio estimation, a salinity estimation, or any combination thereof. The control system may utilize the received data from the water analysis device 102 to control aspects of the oil and/or gas extraction system. For example, the control system may adjust operation of one or more components of the oil and/or gas extraction system based on the received data from the water analysis device 102.

The measurement data generated by the water analysis device 102 may be utilized to train models (e.g., machine learning models) for determination of water salinity, fluid classification, and/or water in liquid ratio estimation. As used herein, "fluid" refers to a single-phase fluid or a heterogeneous mixture of multiple fluid phases, which may include a water phase, an oil or condensate phase, and/or a gas phase. As used herein, "water in liquid ratio" refers to a ratio between a volumetric flow rate of water in a fluid and a total volumetric flow rate of liquid in a fluid. As used herein, "salinity" refers to an amount of salt dissolved in water. As used herein, "fluid classification" refers to flow classes associated with flow regimes and/or heterogeneous mixing properties in a fluid, such as a multiphase, water-continuous flow class; a multiphase, oil-continuous flow class; a wet-gas, water-continuous flow class; a wet-gas, oil-continuous flow class; and so forth. As used herein, "oil-continuous" refers to water being dispersed in the oil phase, while "water-continuous" refers to oil being dispersed in the water phase. The flow classes may include subsets, such as dry gas, oil, gas-dominated and oil (e.g., gas with oil, gas with an oil-continuous liquid, gas with an oil-continuous liquid and a small amount of water, gas with an undetectable amount of water, and so forth), gas-dominated flow with water-enriched liquid (e.g., gas-dominated with oil-continuous liquid, gas-dominated with water-continuous liquid, and so forth), liquid-dominated flow with a separated gas phase (e.g., oil-continuous liquid with gas, water-continuous liquid with gas, and so forth), liquid-dominated flow (e.g., oil-continuous liquid, water-continuous liquid, and so forth), and a transition phase between oil-continuous liquid and water-continuous liquid. In certain instances, oil-continuous liquid may include a water in liquid ratio value less than sixty percent (e.g., less than fifty percent, less than twenty-five percent, less than twenty percent, less than five percent, and so forth). In some instances, water-continuous liquid may include a water in liquid ratio value greater than seventy percent (e.g., greater than seventy-five percent, greater than eighty percent, greater than ninety percent, and so forth). In certain instances, gas-dominated flows may include a GVF value greater than eighty percent (e.g., greater than ninety percent, greater than ninety-five percent, and so forth).

Each of FIGS. 2-8 described below illustrates a respective process for training and/or utilizing a model. Any suitable computer device (e.g., a processor-based controller), such as the processor 120, may perform the processes. In some embodiments, each of the processes may be implemented by executing instructions stored in a tangible, non-transitory, computer-readable medium, such as the memory 122, using the processor 120. For example, the processes may be performed at least in part by one or more software components, such as an operating system of the water analysis device 102, one or more software applications of the water analysis device 102, and the like. While each of the processes is described using steps in a specific sequence, additional steps may be performed, the described steps may be performed in different sequences than the sequence illustrated, and certain described steps may be skipped or not performed altogether. Further still, the steps of any of the respective methods may be performed in parallel with one another, such as at the same time, and/or in response to one another.

Figure 2:
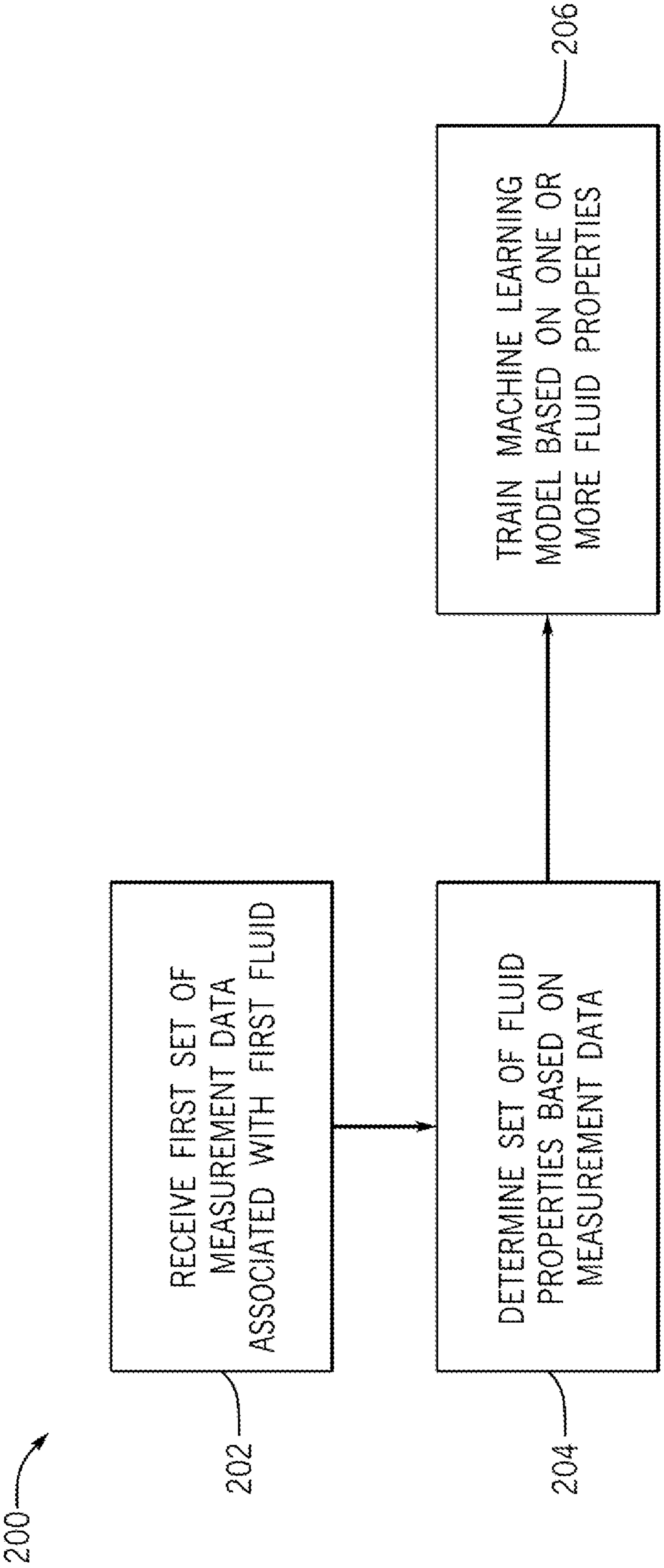
FIG. 2 is a flowchart of an example process for training a model to determine fluid classification, according to an embodiment of the present disclosure.

With the foregoing in mind, FIG. 2 is a flowchart of an example process 200 for training a model (e.g., machine learning model) to determine fluid classification, according to an embodiment of the present disclosure. At block 202, a first set of measurement data is received or collected, such as via the sensor 106 and/or the processor 120. In certain embodiments, any number of measurement data sets may be provided to the processor 120. For example, any number of historical measurement data sets may be utilized to train the model. The measurement data may include, for example, any number of permittivity measurements and/or conductivity measurements associated with a corresponding fluid. At block 204, the processor 120 may determine a set of fluid properties based on the first set of measurement data. As described herein, the processor 120 may determine maximum values, minimum values, average values, standard deviation values, difference values, ratio values, GVF values, and so forth based on the first set of measurement data. Alternatively, one or more of the measurement data sets may include the set of fluid properties.

At block 206, the set of fluid properties may be provided to the model and the model may be trained based on one or more of the fluid properties. In certain embodiments, the set of fluid properties may be analyzed to identify trends associated with one or more fluid properties and one or more fluid classifications. Accordingly, the process 200 may be able to identify patterns associated with the fluid classifications and build a mathematical model of the fluid classification patterns. In some embodiments, the process 200 may identify threshold fluid property values associated with one or more fluid classifications. For example, the process 200 may determine a first fluid classification includes a threshold permittivity value (e.g., threshold maximum permittivity value, threshold minimum permittivity value, threshold average permittivity value, and the like). As such, the process 200 may determine threshold values for classifying fluids. As measurement data is received and analyzed, the measurement data may be compared to the threshold values to identify a fluid classification. The trained model may output the fluid classification (e.g., dry gas, oil, gas-dominated with oil, gas-dominated with oil-continuous liquid, gas-dominated with water-continuous liquid, oil-continuous liquid with gas, water-continuous liquid with gas, oil-continuous liquid, water-continuous liquid, transition phase, and so forth) for a set of measurement data. For example, the trained model may receive new measurement data associated with a new fluid and may determine a fluid classification associated with the new fluid. In some embodiments, the trained model may determine any number of fluid classification probabilities, each classification probability indicative that the new fluid correlates with a particular fluid classification. Additionally, the processor 120 may select a classification probability. For example, the processor 120 may select the highest classification probability. Further, as measurement data is collected, new measurement data may be added to the historical measurement data sets, increasing the size of the measurement data used to train the model. As such, the model may be retrained based on new measurement data on an iterative or rolling basis. Additionally, the process 200 may be configured to analyze collected measurement data and update the threshold values accordingly.

Figure 3:
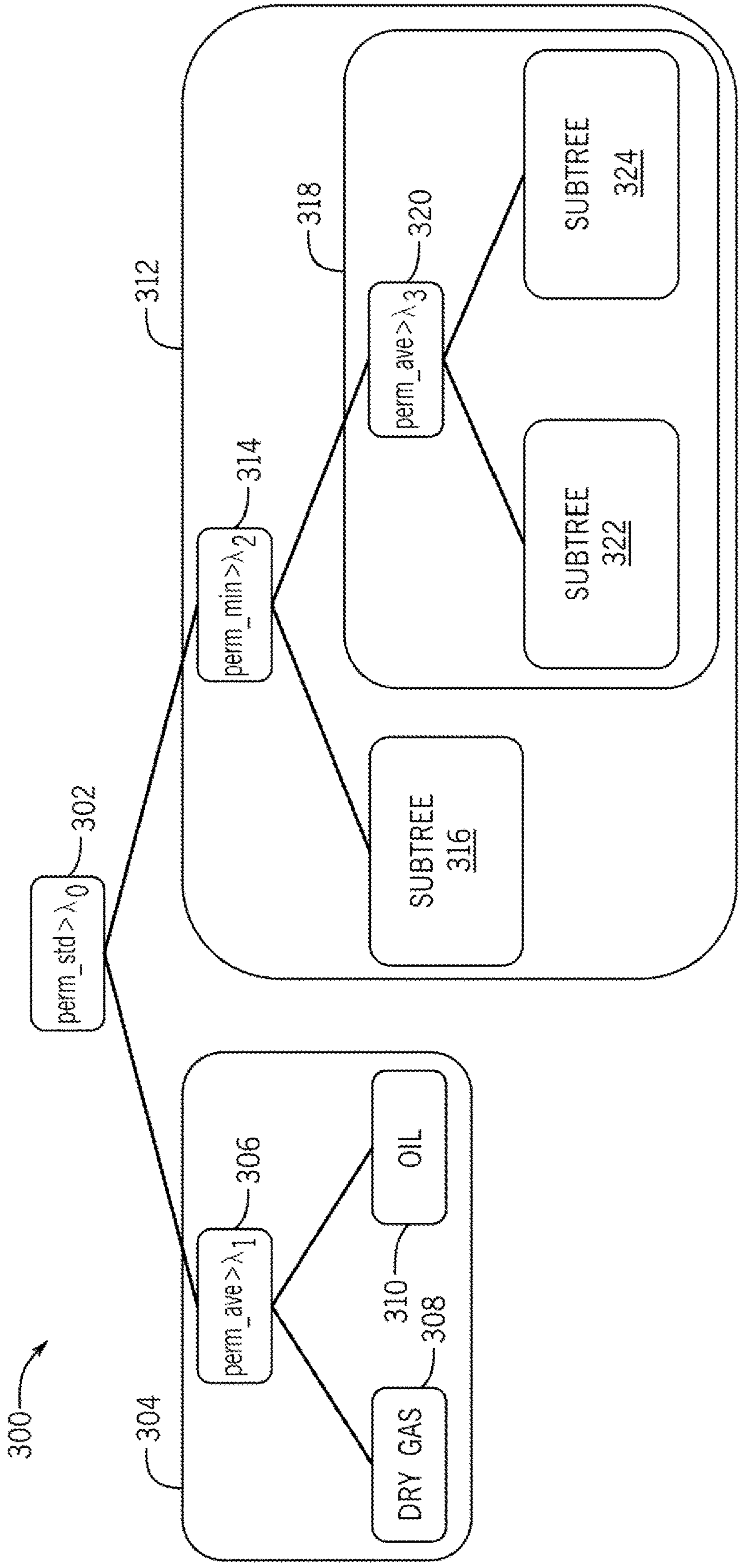
FIG. 3 is a flowchart of a model for classifying a fluid, according to an embodiment of the present disclosure.

FIG. 3 is a flowchart of a model 300 (e.g., a computer-based model) for classifying a fluid, according to an embodiment of the present disclosure. The model 300 may include a decision tree that may include any number of nodes for determining a classification of a fluid. At a node of the decision tree, one or more fluid properties may be compared with a corresponding threshold property value. Based on the comparison, a branch of the decision tree may be followed to a subsequent node. Nodes and branches of the decision tree may be progressed through until a terminal node associated with any number of fluid classification probabilities is reached. As such, the model 300 may identify a fluid classification for a fluid based on any number of comparisons between one or more fluid properties and one or more corresponding threshold property values. As shown in FIG. 3, a first node 302 may compare a first fluid property value and a corresponding first threshold property value. The first node 302 may be a threshold decision node. For example, the first node 302 may compare a permittivity standard deviation value associated with the fluid and a threshold permittivity standard deviation value. Dry gas and oil may include lower standard deviations for permittivity and/or conductivity in comparison to other fluid classifications. As such, the model 300 may include a first subtree 304 down a first branch from the first node 302 based on the permittivity standard deviation value falling within the threshold permittivity standard deviation value.

The first subtree 304 may include any number of additional nodes (e.g., terminal nodes, threshold decision nodes, subtrees, and so forth), branches, and/or subtrees for determining the fluid classification. For example, a second node 306 may compare an average permittivity value and a first threshold average permittivity value. Dry gas may correlate with lower average permittivity values. As such, the first subtree 304 may include a first terminal node 308 corresponding to the average permittivity value falling within the first threshold average permittivity value. The first terminal node 308 may correspond to a dry gas fluid classification. As such, the model 300 may output dry gas as the fluid classification upon reaching the first terminal node 308. Additionally, the first subtree 304 may include a second terminal node 310 corresponding to the average permittivity value meeting or exceeding the first threshold average permittivity value. The second terminal node 310 may correspond to an oil fluid classification. Accordingly, the model 300 may output oil as the fluid classification upon reaching the second terminal node 310.

Returning to the first node 302, the model 300 may include a second subtree 312 down a second branch from the first node 302 based on the permittivity standard deviation value meeting or exceeding the threshold permittivity standard deviation value. The second subtree 312 may include any number of additional nodes and/or branches for determining the fluid classification. For example, a third node 314 may compare a minimum permittivity value and a threshold minimum permittivity value. The second subtree 312 may include a third subtree 316 based on the minimum permittivity value falling within the threshold minimum permittivity value. The third subtree 316 may assist in determining the fluid classification and may include any number of nodes, branches, and/or subtrees. For example, the third subtree 316 may include any number of terminal nodes. Based on the minimum permittivity value meeting or exceeding the threshold minimum permittivity value, the classification process may proceed down a second branch from the third node 314 to a fourth subtree 318. The fourth subtree 318 may include any number of nodes, branches, and/or subtrees. For example, the fourth subtree 318 may include a fourth node 320 that may compare the average permittivity value and a second threshold average permittivity value. In some embodiments, the second threshold average permittivity value may be different (e.g., lower, greater) from the first threshold average permittivity value. Alternatively, the second threshold average permittivity value may be the same as the first threshold average permittivity value. The fourth subtree 318 may include a fifth subtree 322 and a sixth subtree 324. The fifth subtree 322 and sixth subtree 324 may include any number of nodes, such as terminal nodes, branches, and/or subtrees. The process may proceed down a first branch from the fourth node 320 to the fifth subtree 322 based on the average permittivity value falling within the second threshold average permittivity value. Alternatively, the process may proceed down a second branch from the fourth node 320 to the sixth subtree 324 based on the average permittivity value meeting or exceeding the second threshold average permittivity value.

The model 300 may include at least one terminal node associated with each fluid classification, such as a multiphase, water-continuous flow class; a multiphase, oil-continuous flow class; a wet-gas, water-continuous flow class; a wet-gas, oil-continuous flow class; and so forth. The flow classes may include subsets, such as dry gas, oil, gas-dominated and oil (e.g., gas with oil, gas with an oil-continuous liquid, gas with an oil-continuous liquid and a small amount of water, gas with an undetectable amount of water, and so forth), gas-dominated flow with water-enriched liquid (e.g., gas-dominated with oil-continuous liquid, gas-dominated with water-continuous liquid, and so forth), liquid-dominated flow with a separated gas phase (e.g., oil-continuous liquid with gas, water-continuous liquid with gas, and so forth), liquid-dominated flow (e.g., oil-continuous liquid, water-continuous liquid, and so forth), and a transition phase between oil-continuous liquid and water-continuous liquid. As such, upon reaching any of the terminal nodes, the model 300 may output the fluid classification corresponding to the terminal node. Accordingly, the model 300 may classify the fluid based on any number of fluid property comparisons. While specific fluid property values are described above with respect to the model 300, different and/or additional fluid property values may be compared at any node of the model 300. Additionally or alternatively, any number of nodes included in the model 300 may be associated with the same fluid property and/or the same or similar set of fluid properties. For example, a previous node may compare an average conductivity value and a first threshold average conductivity value and a subsequent node may compare the average conductivity value and a second threshold average conductivity value. As such, the model 300 may include any number of threshold values for each fluid property.

Figure 4:
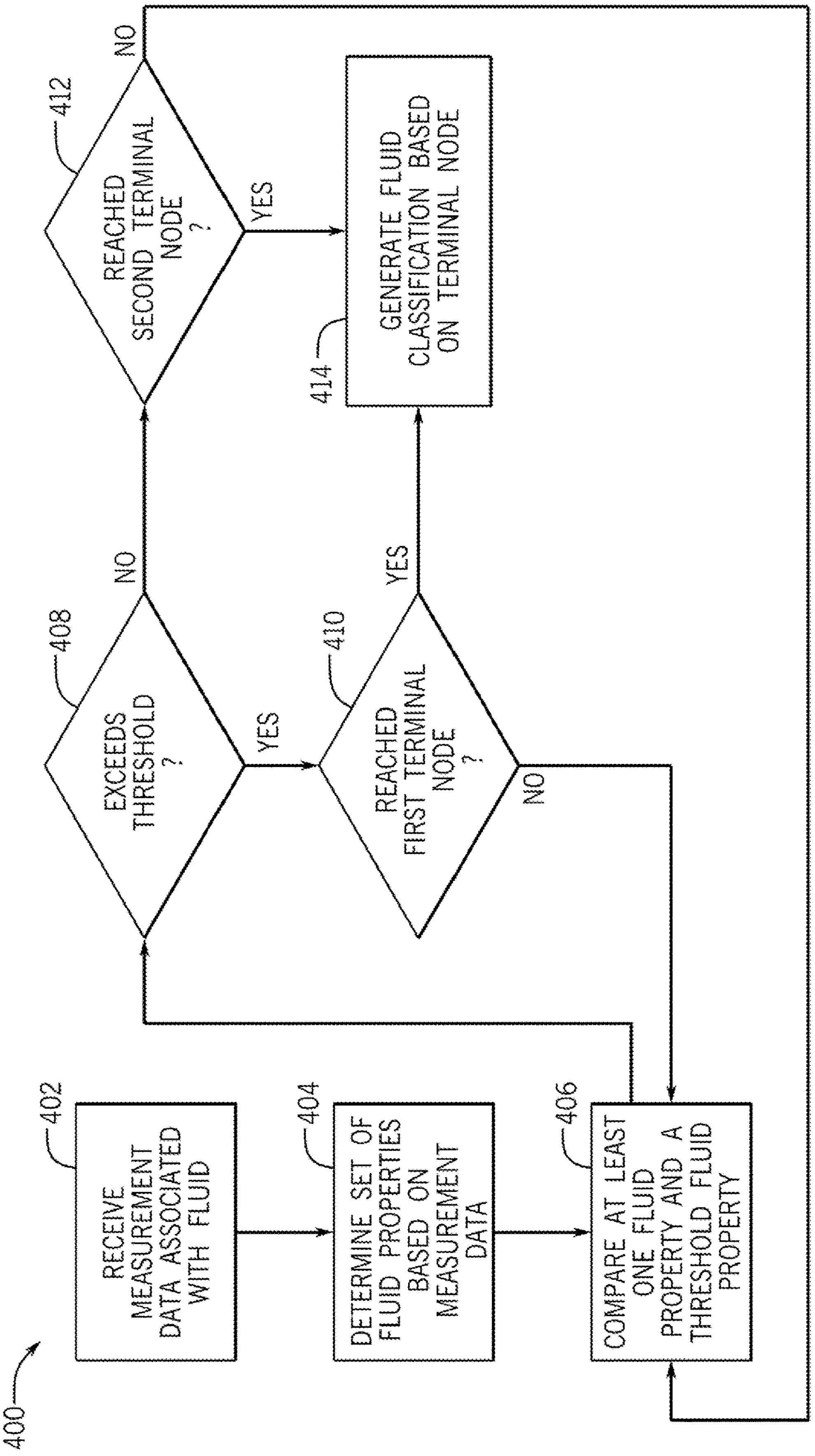
FIG. 4 is a flowchart of an example process for classifying a fluid using the model of FIG. 3, according to an embodiment of the present disclosure.

With the foregoing in mind, FIG. 4 is a flowchart of an example process 400 for classifying a fluid utilizing a model (e.g., machine learning model, such as model 300), according to an embodiment of the present disclosure. At block 402, measurement data is received or collected, such as via the sensor 106 and/or the processor 120. In certain embodiments, any number of measurement data sets may be provided to the processor 120. For example, any number of measurement data sets may be classified using the model. Each measurement data set may include, for example, any number of permittivity measurements and/or conductivity measurements associated with a corresponding fluid. At block 404, the processor 120 may determine a set of fluid properties based on the first set of measurement data. As described herein, the processor 120 may determine maximum values, minimum values, average values, standard deviation values, difference values, ratio values, GVF values, and so forth based on the first set of measurement data. Alternatively, one or more of the measurement data sets may include the set of fluid properties.

At block 406, the model may compare at least one fluid property and a corresponding threshold fluid property, as described herein. At block 408, the model may determine whether the fluid property exceeds the threshold fluid property. Based on the fluid property exceeding the threshold fluid property (YES path of block 408), the processor 120 may continue along another branch of the model 300 to a node (e.g., threshold decision node, terminal node, subtree, and so forth) of the model 300. The processor 120 may determine (block 410) whether a first terminal node in the model 300 is reached. In some embodiments, the processor 120 may reach a first terminal node (YES path of block 410) and may determine a first set of fluid classification probabilities, each fluid classification probability associated with a corresponding fluid classification, such as dry gas and/or oil. In some embodiments, the model may reach a node and/or a subtree associated with any number of fluid classifications. For example, the model may reach a node associated with multiple fluid classifications. Accordingly, the model may determine the first set of fluid classification probabilities (e.g., 0%, 10%, 25%, and so forth). Additionally or alternatively, the model may reach a terminal node, such as first terminal node 308, and may output the highest fluid classification probability (e.g., a dry gas fluid classification probability). In certain embodiments, a terminal node may correspond with a fluid classification probability (e.g., 75%, 80%, 90%, 95%, and so forth) associated with a corresponding fluid classification, such as dry gas, oil, oil-continuous liquid, and so forth.

The process 400 may continue and the processor 120 may determine whether the fluid is classified. For example, the processor 120 may reach a first terminal node in the model 300 associated with any number of fluid classification probabilities. The processor 120 may generate (block 414) a first set of fluid classification probabilities based on the first terminal node. For example, the terminal node may correspond to any number of fluid classification probabilities, each fluid classification probability associated with a corresponding fluid. The processor 120 may determine and/or receive the fluid classification probabilities based on the reached terminal node. Accordingly, the processor 120 may select the fluid classification that corresponds to the highest fluid classification probability. The processor 120 may generate (e.g., output, present, display, and the like) (block 414) the selected fluid classification associated with the fluid.

In response to not reaching a terminal node (NO path of block 410), the processor 120 may return to block 406 to compare another fluid property, such as average conductivity, and another corresponding threshold fluid property, such as a threshold average conductivity. In some embodiments, the processor 120 may compare the same fluid property and a second threshold fluid property, a subsequent fluid property and a subsequent threshold fluid property, an additional fluid property and an additional threshold fluid property, and so forth.

In response to the at least one fluid property failing to meet or exceed the threshold fluid property (NO path of block 408), the processor 120 may continue to step 412 to determine whether a second terminal node was reached in the model 300. The second terminal node may correspond to a second set of fluid classification probabilities, each fluid classification probability associated with a corresponding fluid classification. The second set of fluid classification probabilities may correspond to a second set of fluid classifications, such as gas-dominated with oil, gas-dominated with oil-continuous liquid, and so forth. In certain embodiments, the second set of fluid classifications may differ from the first set of fluid classifications. Based on the fluid property failing to meet or exceed the threshold fluid property (NO path of block 408), the processor 120 may continue along another branch of the model 300 to a node (e.g., threshold decision node, terminal node, subtree, and so forth) of the model 300. The processor 120 may determine (block 412) whether a second terminal node in the model 300 is reached. In some embodiments, the processor 120 may reach a second terminal node (YES path of block 412) and may determine the second set of fluid classification probabilities, each fluid classification probability associated with a corresponding fluid classification, such as dry gas and/or oil. In some embodiments, the model may reach a node and/or a subtree associated with any number of fluid classifications. For example, the model may reach a node associated with multiple fluid classifications. Accordingly, the model may determine the second set of fluid classification probabilities (e.g., 0%, 10%, 25%, and so forth). Additionally or alternatively, the model may reach a terminal node, such as first terminal node 308, and may output the highest fluid classification probability (e.g., a dry gas fluid classification probability). In certain embodiments, a terminal node may correspond with a fluid classification probability (e.g., 75%, 80%, 90%, 95%, and so forth) associated with a corresponding fluid classification, such as dry gas, oil, oil-continuous liquid, and so forth.

The process 400 may continue and the processor 120 may determine whether the fluid is classified. For example, the processor 120 may reach the second terminal node in the model 300 associated with any number of fluid classification probabilities. The processor 120 may generate (block 414) the second set of fluid classification probabilities based on the second terminal node. For example, the terminal node may correspond to any number of fluid classification probabilities, each fluid classification probability associated with a corresponding fluid. The processor 120 may determine and/or receive the fluid classification probabilities based on the reached terminal node. Accordingly, the processor 120 may select the fluid classification that corresponds to the highest fluid classification probability. The processor 120 may generate (e.g., output, present, display, and the like) (block 414) the selected fluid classification associated with the fluid. In response to not reaching a second terminal node (NO path of block 412), the processor 120 may return to block 406 to compare another fluid property and another corresponding threshold fluid property.

As such, the process 400 may be utilized to classify a fluid based on measurement data, such as conductivity, permittivity, and so forth. The process 400 may utilize a trained model (e.g., machine learning model, such as model 300) to classify the fluid according to any number of fluid classifications, such as dry gas, oil, oil-continuous liquid, water-continuous liquid, and so forth. The process 400 may be implemented by any suitable computing device, such as processor 120. The fluid classification may be utilized as a water property input to a flow meter, such as a multiphase flow meter. For example, the multiphase flow meter may receive the fluid classification output by the process 400 (e.g., model 300) and may utilize the fluid classification in determining individual phase flow rates (e.g., water flow rate, gas flow rate, oil flow rate, and so forth) associated with a fluid. Additionally or alternatively, the flow rates determined by the multiphase flow meter may be utilized to facilitate reservoir management and detection of formation water breakthrough.

Figure 5:
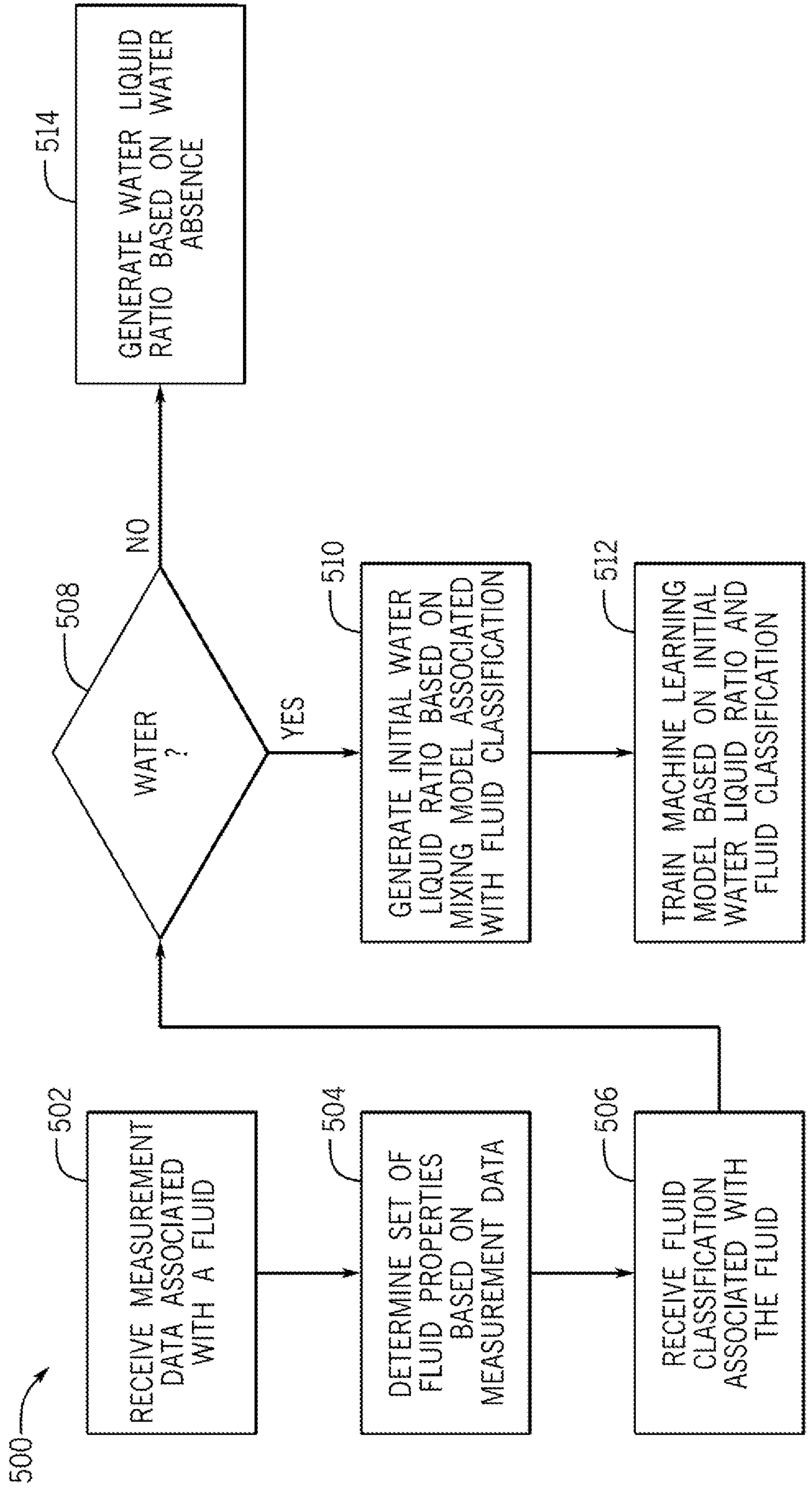
FIG. 5 is a flowchart of an example process for training a model to determine a water in liquid ratio for a fluid, according to an embodiment of the present disclosure.

FIG. 5 is a flowchart of an example process 500 for training a water in liquid ratio model (e.g., machine learning model, such as a regression model) to determine a water in liquid ratio for a fluid, according to an embodiment of the present disclosure. At block 502, a first set of measurement data is received or collected, such as via the sensor 106 and/or the processor 120. In certain embodiments, any number of measurement data sets may be provided to the processor 120. For example, any number of historical measurement data sets may be utilized to train the water in liquid ratio model. The measurement data may include, for example, any number of permittivity measurements and/or conductivity measurements associated with a corresponding fluid. At block 504, the processor 120 may determine a set of fluid properties based on the first set of measurement data. As described herein, the processor 120 may determine maximum values, minimum values, average values, standard deviation values, difference values, ratio values, GVF values, and so forth based on the first set of measurement data. Alternatively, one or more of the measurement data sets may include the set of fluid properties.

At block 506, the processor 120 may receive and/or collect fluid classification data associated with the set of fluid properties. The fluid classifications may include a multiphase flow that is liquid-dominated (e.g., water-continuous liquid with or without gas, oil-continuous liquid with or without gas), wet gas flow (gas-dominated with oil, gas-dominated with oil-continuous liquid, gas-dominated with water-continuous liquid), dry gas, oil, a transition phase, and so forth. In certain embodiments, the fluid classification data may include any number of fluid classifications, each fluid classification associated with a corresponding set of fluid properties and a corresponding fluid. At block 508, the processor 120 may determine a presence of water for any number of the set of fluid properties based on the classification data. For example, the multiphase, liquid-dominated flow and wet gas flow may include water. As such, the processor 120 may determine (YES path of block 508) that the fluid includes water.

At block 510, the processor 120 may generate an initial water in liquid ratio estimation based on a mixing model (e.g., a computer-based mixing model). The mixing model may include a two-phase mixing model for heterogeneous mixtures. A mixing model may be selected based on the fluid classification. For example, a water-continuous liquid fluid classification may utilize a first mixing model (e.g., first computer-based mixing model) and an oil-continuous liquid may utilize a second mixing model (e.g., second computer-based mixing model). The mixing model may output the initial water in liquid ratio estimation. At block 512, the processor 120 may provide the set of fluid properties, the fluid classification, and the initial water in liquid ratio estimation to the water in liquid ratio model and the water in liquid ratio model may be trained based on the data set. In certain embodiments, the data set may be analyzed to identify trends associated with one or more fluid properties, one or more fluid classifications, and one or more initial water in liquid ratio estimations. Accordingly, the process 500 may be able to identify patterns associated with the data set and build a mathematical water in liquid ratio model of the water in liquid ratio calculation. The trained water in liquid ratio model may output an improved water in liquid ratio estimation based on the data set. For example, the trained model may receive a new data set associated with a new fluid and may determine an improved water in liquid ratio estimation associated with the new fluid. In some embodiments, the trained model may determine any number of water in liquid ratio estimations for any number of fluids. Further, as measurement data is collected, new data sets may be added to the historical data sets, increasing the size of the measurement data used to train the model. As such, the model may be retrained based on new data sets on an iterative or rolling basis. Additionally, the process 500 may be configured to analyze collected data sets and update the models accordingly.

Alternatively, the processor 120 may determine (NO path of block 508) the fluid lacks water based on the fluid classification. For example, the oil fluid classification and the dry gas fluid classification may lack water or include an inconsequential amount of water. Accordingly, the oil fluid classification and dry gas fluid classification may have a water in liquid ratio of zero. As such, the processor 120 may generate (block 514) the water in liquid ratio for the oil fluid classification or the dry gas fluid classification.

Figure 6:
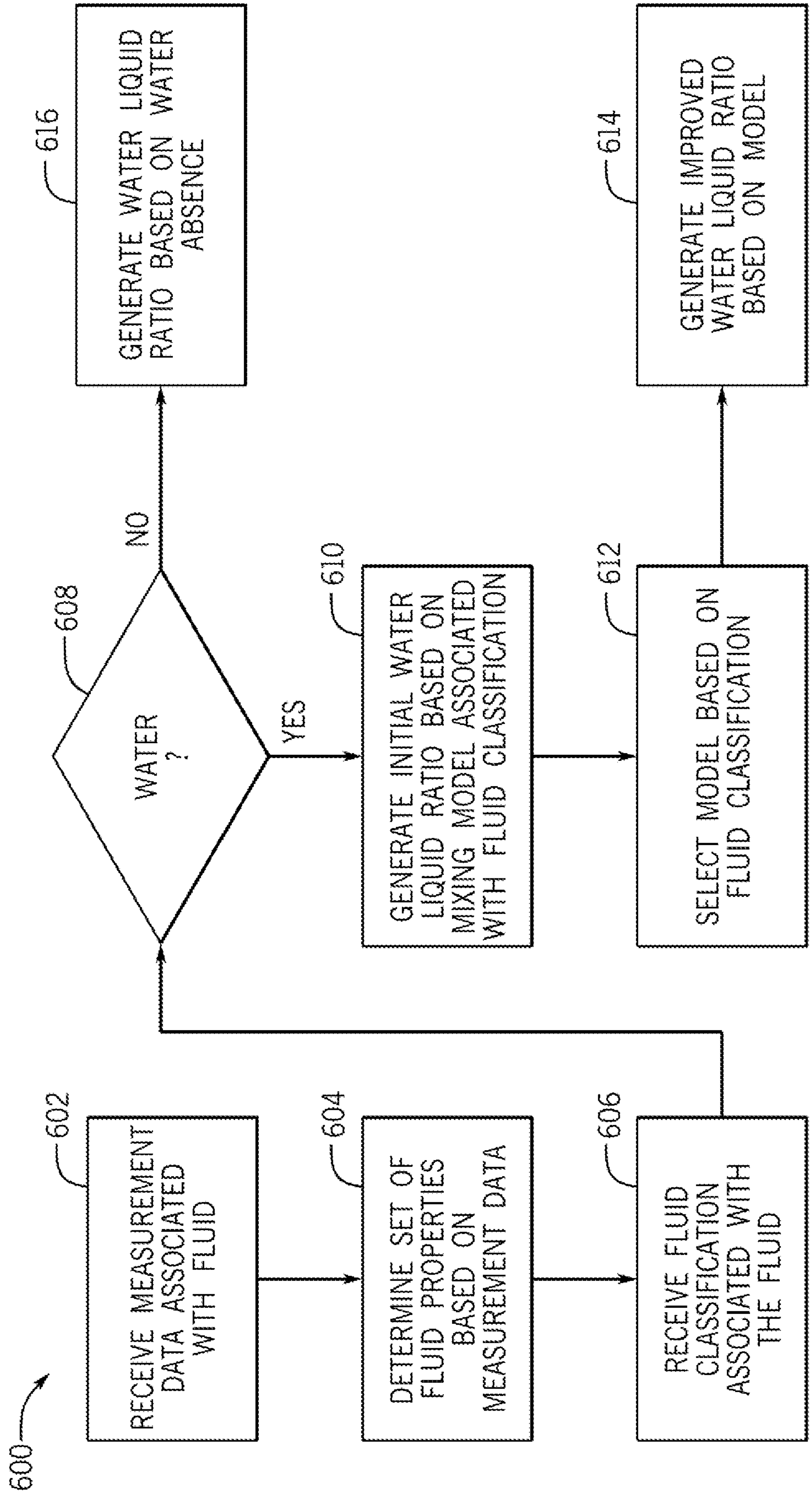
FIG. 6 is a flowchart of an example process for determining a water in liquid ratio for a fluid, according to an embodiment of the present disclosure.

With the foregoing in mind, FIG. 6 is a flowchart of an example process 600 for determining a water in liquid ratio for a fluid utilizing the trained water in liquid ratio model of FIG. 5, according to an embodiment of the present disclosure. At block 602, a first set of measurement data is received or collected, such as via the sensor 106 and/or the processor 120. In certain embodiments, any number of measurement data sets may be provided to the processor 120 for determining an improved water in liquid ratio. The measurement data may include, for example, any number of permittivity measurements and/or conductivity measurements associated with a corresponding fluid. At block 604, the processor 120 may determine a set of fluid properties based on the first set of measurement data. As described herein, the processor 120 may determine maximum values, minimum values, average values, standard deviation values, difference values, ratio values, GVF values, and so forth based on the first set of measurement data. Alternatively, one or more of the measurement data sets may include the set of fluid properties.

At block 606, the processor 120 may receive and/or collect fluid classification data associated with the set of fluid properties. The fluid classifications may include a multiphase flow that is liquid-dominated (e.g., water-continuous liquid with or without gas, oil-continuous liquid with or without gas), wet gas flow (gas-dominated with oil, gas-dominated with oil-continuous liquid, gas-dominated with water-continuous liquid), dry gas, oil, a transition phase, and so forth. In certain embodiments, the fluid classification data may include any number of fluid classifications, each fluid classification associated with a corresponding set of fluid properties and a corresponding fluid. Additionally or alternatively, the measurement data may include the fluid classification data. At block 608, the processor 120 may determine a presence of water for any number of the set of fluid properties based on the classification data. For example, the multiphase, liquid-dominated flow and wet gas flow may include water. As such, the processor 120 may determine (YES path of block 608) the fluid includes water.

At block 610, the processor 120 may generate an initial water in liquid ratio estimation based on a mixing model. The mixing model may include a two-phase mixing model for heterogeneous mixtures. A mixing model may be selected based on the fluid classification. For example, a water-continuous liquid fluid classification may utilize a first mixing model and an oil-continuous liquid may utilize a second mixing model. The mixing model may output the initial water in liquid ratio estimation. At block 612, the processor 120 may select a water in liquid ratio model (e.g., machine learning model, computer-based model) based on the fluid classification. The selected water in liquid ratio model may be utilized to generate (block 614) an improved water in liquid ratio estimation.

Alternatively, the processor 120 may determine (NO path of block 608) the fluid lacks water based on the fluid classification. For example, the oil fluid classification and the dry gas fluid classification may lack water or include an inconsequential amount of water. Accordingly, the oil fluid classification and dry gas fluid classification may have a water in liquid ratio of zero. As such, the processor 120 may generate (block 616) the water in liquid ratio for the oil fluid classification or the dry gas fluid classification.

Figure 7:
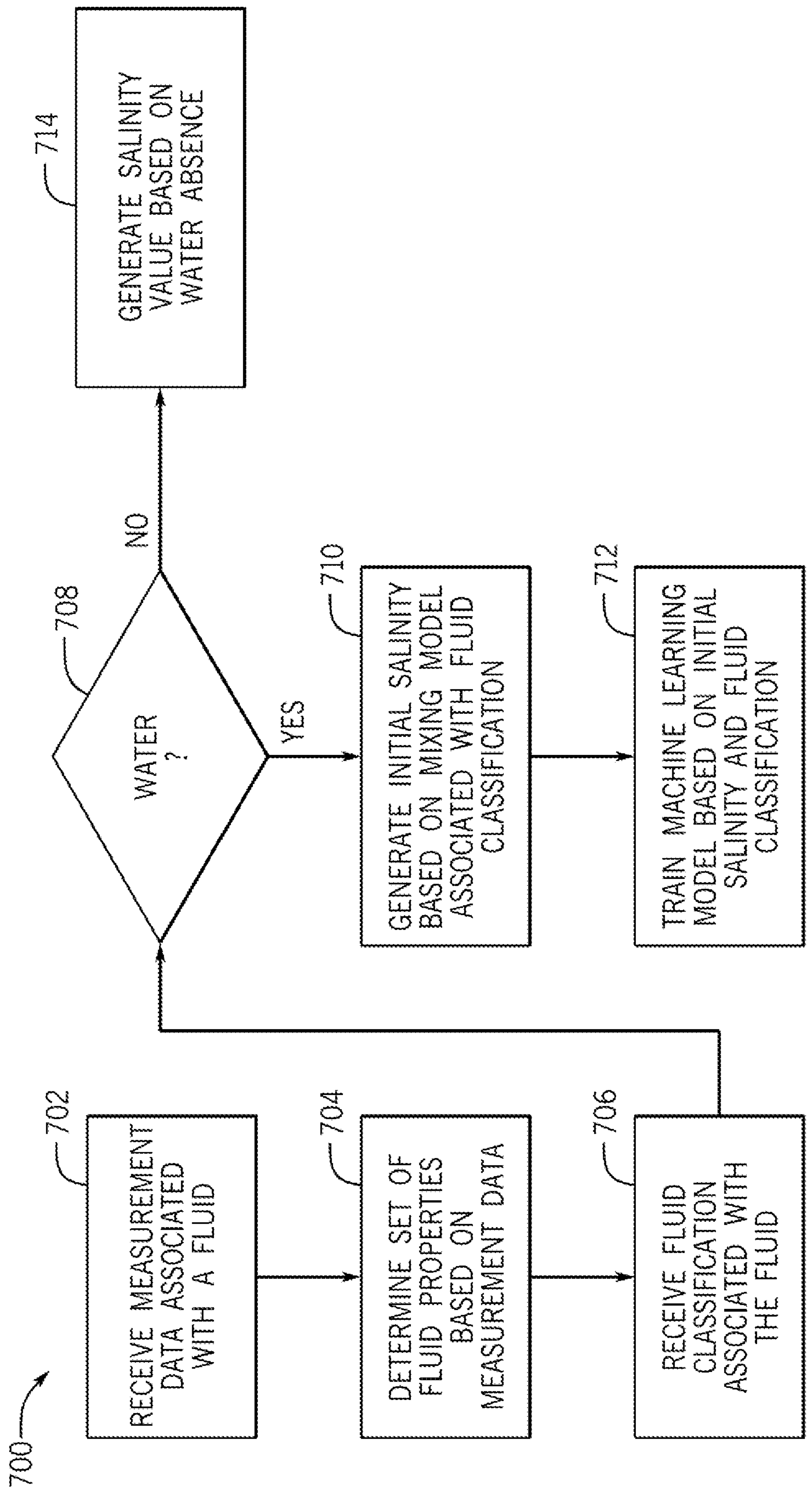
FIG. 7 is a flowchart of an example process for training a model to determine a salinity for a fluid, according to an embodiment of the present disclosure.

FIG. 7 is a flowchart of an example process 700 for training a salinity model (e.g., machine learning model) to determine a salinity for a fluid, according to an embodiment of the present disclosure. At block 702, a first set of measurement data is received or collected, such as via the sensor 106 and/or the processor 120. In certain embodiments, any number of measurement data sets may be provided to the processor 120. For example, any number of historical measurement data sets may be utilized to train the salinity model. The measurement data may include, for example, any number of permittivity measurements and/or conductivity measurements associated with a corresponding fluid. At block 704, the processor 120 may determine a set of fluid properties based on the first set of measurement data. As described herein, the processor 120 may determine maximum values, minimum values, average values, standard deviation values, difference values, ratio values, GVF values, and so forth based on the first set of measurement data. Alternatively, one or more of the measurement data sets may include the set of fluid properties.

At block 706, the processor 120 may receive and/or collect fluid classification data associated with the set of fluid properties. The fluid classifications may include a multiphase flow that is liquid-dominated (e.g., water-continuous liquid with or without gas, oil-continuous liquid with or without gas), wet gas flow (gas-dominated with oil, gas-dominated with oil-continuous liquid, gas-dominated with water-continuous liquid), dry gas, oil, a transition phase, and so forth. In certain embodiments, the fluid classification data may include any number of fluid classifications, each fluid classification associated with a corresponding set of fluid properties and a corresponding fluid. At block 708, the processor 120 may determine a presence of water for any number of the set of fluid properties based on the classification data. For example, the multiphase, liquid-dominated flow and wet gas flow may include water. As such, the processor 120 may determine (YES path of block 708) the fluid includes water.

At block 710, the processor 120 may generate an initial salinity estimation based on a mixing model. The mixing model may include a two-phase mixing model for a water-continuous liquid. The mixing model may be selected based on the fluid classification. For example, a water-continuous liquid fluid classification may utilize a first mixing model and an oil-continuous liquid may utilize a second mixing model. The mixing model may output the initial salinity estimation. At block 712, the processor 120 may provide the set of fluid properties, the fluid classification, and the initial salinity estimation to the salinity model and the salinity model may be trained based on the data set. In certain embodiments, the data set may be analyzed to identify trends associated with one or more fluid properties, one or more fluid classifications, and one or more initial salinity estimations. Accordingly, the process 700 may be able to identify patterns associated with the data set and build a mathematical salinity model of the salinity calculation. The trained salinity model may output an improved salinity estimation based on the data set. For example, the trained model may receive a new data set associated with a new fluid and may determine an improved salinity estimation associated with the new fluid. In some embodiments, the trained salinity model may determine any number of salinity estimations for any number of fluids, each salinity estimation associated with a corresponding fluid. Further, as measurement data is collected, new data sets may be added to the historical data sets, increasing the size of the measurement data used to train the model. As such, the salinity model may be retrained based on new data sets on an iterative or rolling basis. Additionally, the process 700 may be configured to analyze collected data sets and update the salinity models accordingly.

Alternatively, the processor 120 may determine (NO path of block 708) the fluid lacks water based on the fluid classification. For example, the oil fluid classification and the dry gas fluid classification may lack water or include an inconsequential amount of water. Accordingly, the oil fluid classification and dry gas fluid classification may have a salinity of zero. As such, the processor 120 may generate (block 714) the salinity value for the oil fluid classification or the dry gas fluid classification.

Figure 8:
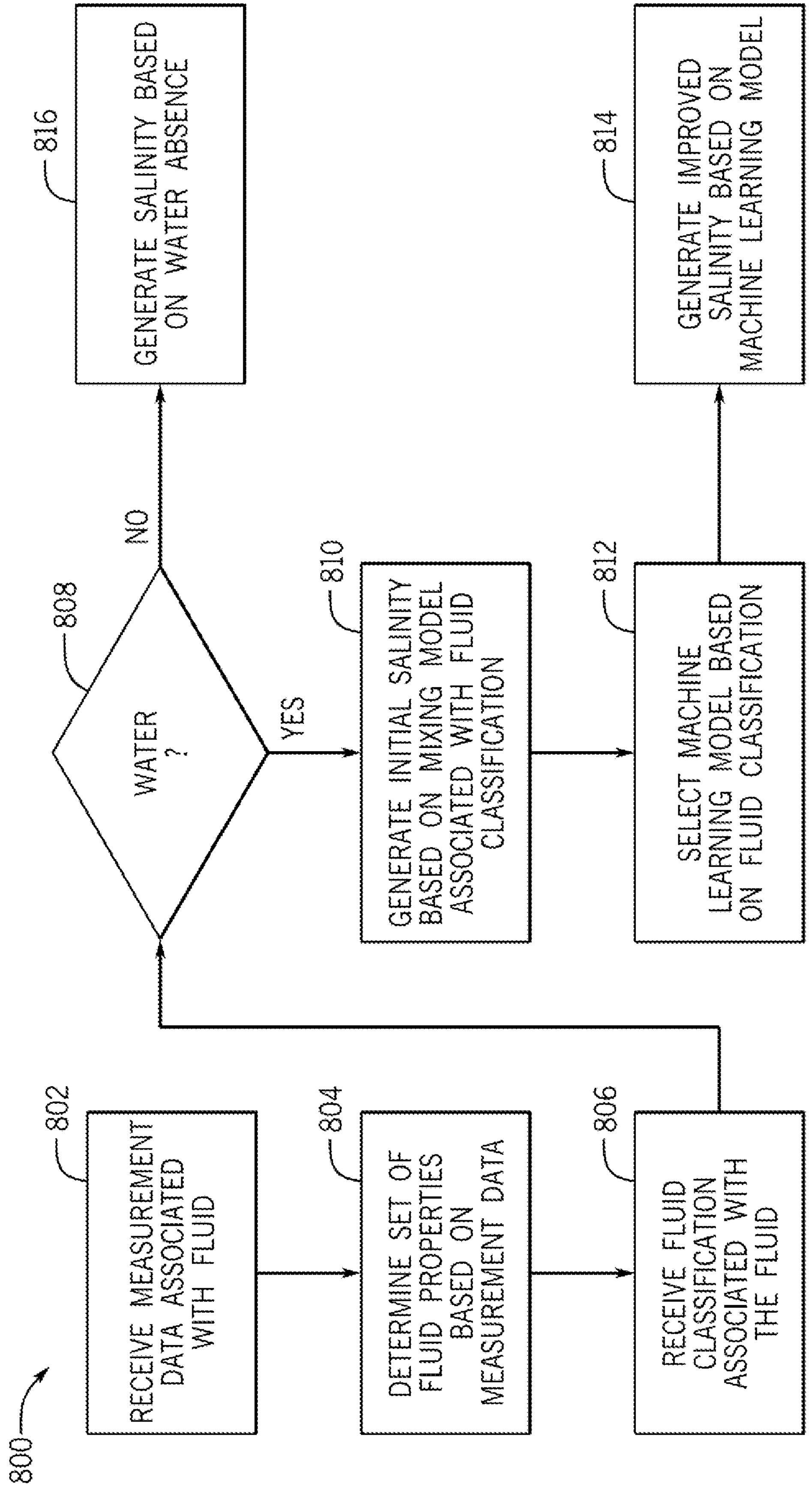
FIG. 8 is a flowchart of an example process for determining a salinity for a fluid, according to an embodiment of the present disclosure.

With the foregoing in mind, FIG. 8 is a flowchart of an example process 800 for determining a salinity value for a fluid utilizing the trained salinity model of FIG. 7, according to an embodiment of the present disclosure. At block 802, a first set of measurement data is received or collected, such as via the sensor 106 and/or the processor 120. In certain embodiments, any number of measurement data sets may be provided to the processor 120 for determining an improved salinity value. The measurement data may include, for example, any number of permittivity measurements and/or conductivity measurements associated with a corresponding fluid. At block 804, the processor 120 may determine a set of fluid properties based on the first set of measurement data. As described herein, the processor 120 may determine maximum values, minimum values, average values, standard deviation values, difference values, ratio values, GVF values, and so forth based on the first set of measurement data. Alternatively, one or more of the measurement data sets may include the set of fluid properties.

At block 806, the processor 120 may receive and/or collect fluid classification data associated with the set of fluid properties. The fluid classifications may include a multiphase flow that is liquid-dominated (e.g., water-continuous liquid with or without gas, oil-continuous liquid with or without gas), wet gas flow (gas-dominated with oil, gas-dominated with oil-continuous liquid, gas-dominated with water-continuous liquid), dry gas, oil, a transition phase, and so forth. In certain embodiments, the fluid classification data may include any number of fluid classifications, each fluid classification associated with a corresponding set of fluid properties and a corresponding fluid. Additionally or alternatively, the measurement data may include the fluid classification data. At block 808, the processor 120 may determine a presence of water for any number of the set of fluid properties based on the classification data. For example, the multiphase, liquid-dominated flow and wet gas flow may include water. As such, the processor 120 may determine (YES path of block 808) the fluid includes water.

At block 810, the processor 120 may generate an initial salinity estimation based on a mixing model. The mixing model may output the initial salinity estimation. At block 812, the processor 120 may select a trained salinity model (e.g., machine learning model) based on the fluid classification. The selected salinity model may be utilized to generate (block 814) an improved salinity estimation.

Alternatively, the processor 120 may determine (NO path of block 808) the fluid lacks water based on the fluid classification. For example, the oil fluid classification and the dry gas fluid classification may lack water or include an inconsequential amount of water. Accordingly, the oil fluid classification and dry gas fluid classification may have a salinity value of zero. As such, the processor 120 may generate (block 816) the salinity value based on the oil fluid classification or the dry gas fluid classification.

Figure 9:
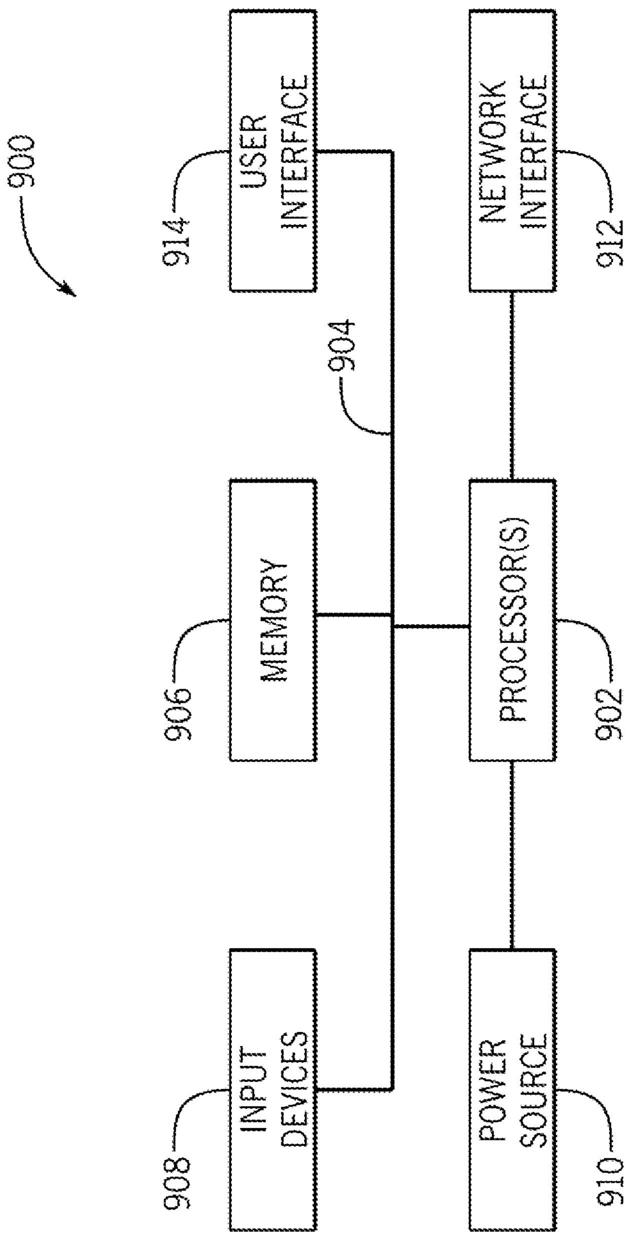
FIG. 9 is a schematic of a computing system, according to an embodiment of the present disclosure.

It may be appreciated that the present approach may be implemented using one or more processor-based systems, such as shown in FIG. 9. For example, such processor-based systems may be utilized in the water analysis device 102, as well as in other components of the system 100 and/or the water analysis device 102. Likewise, applications and/or databases utilized in the present approach may be stored, employed, and/or maintained on such processor-based systems. As may be appreciated, such systems as shown in FIG. 9 may be present in a distributed computing environment, a networked environment, or other multi-computer architecture.

With this in mind, an example computer system may include some or all of the computer components depicted in FIG. 9. FIG. 9 generally illustrates a block diagram of example components of a computing system 900 and their potential interconnections or communication paths, such as along one or more buses. As illustrated, the computing system 900 may include various hardware components such as, but not limited to, one or more processors 902, one or more buses 904, memory 906, input devices 908, a power source 910, a network interface 912, a user interface 914, and/or other computer components useful in performing the functions described herein.

The one or more processors 902 may include one or more microprocessors capable of performing instructions stored in the memory 906. Additionally or alternatively, the one or more processors 902 may include application-specific integrated circuits (ASICs), field-programmable gate arrays (FPGAs), and/or other devices designed to perform some or all of the functions discussed herein without calling instructions from the memory 906.

With respect to other components, the one or more buses 904 include suitable electrical channels to provide data and/or power between the various components of the computing system 900. The memory 906 may include any tangible, non-transitory, and computer-readable storage media. Although shown as a single block in FIG. 9, the memory 906 can be implemented using multiple physical units of the same or different types in one or more physical locations. The input devices 908 correspond to structures to input data and/or commands to the one or more processors 902. For example, the input devices 908 may include a mouse, touchpad, touchscreen, keyboard, and the like. The power source 910 can be any suitable source for power of the various components of the computing system 900, such as line power and/or a battery source. The network interface 912 includes one or more transceivers capable of communicating with other devices over one or more networks (e.g., a communication channel). The network interface 912 may provide a wired network interface or a wireless network interface. A user interface 914 may include a display that is configured to display text or images transferred to it from the one or more processors 902. In addition and/or alternative to the display, the user interface 914 may include other devices for interfacing with a user, such as lights (e.g., LEDs), speakers, and the like.

Any suitable computing device (e.g., a processor-based controller), such as the computing system 900 and/or the one or more processors 902, may perform the processes described in FIGS. 2-8. In some embodiments, each of the processes may be implemented by executing instructions stored in a tangible, non-transitory, computer-readable medium, such as the memory 906, using the one or more processors 902. For example, the processes may be performed at least in part by one or more software components, such as an operating system of the computing system 900, one or more software applications of the computing system 900, and the like. Additionally or alternatively, the processes described in FIGS. 2-8 may be stored in any suitable storage device, such as the memory 906. The memory 906 may store instructions that, when executed by the one or more processors 902, may perform the processes, as described herein. Additionally or alternatively, the models, measurements, historical data, and any combination thereof may be stored in any suitable storage device, such as the memory 906. The computing system 900 (e.g., the one or more processors 902) may train and/or implement any of the models, may receive measurement data, may analyze measurement data, may store measurement data, or any combination thereof. In certain embodiments, the computing system 900 may monitor and/or control components of an oil and/or gas extraction system, such as monitoring and controlling well production, positions of valves, fluid property inputs to wet-gas, multiphase or single-phase flow meters, injection of fluid (e.g., chemicals, such as hydrate inhibitors or scale inhibitors), and the like, for retrieving oil and/or gas from a well.

The technical effects of the systems and methods described in the embodiments of FIGS. 1-9 include the training and utilization of models for classifying fluids, determining water in liquid ratio for fluids, and determining salinity of fluids. The models may be trained using measurement data (e.g., permittivity, conductivity, gas volume fraction) from a water analyzer. The output of the models may be used for determination of other fluid properties. For example, the classification model output (e.g., flow regime classification) may be utilized to train and/or implement a water in liquid ratio model and/or a salinity model. Additionally, the output of the models may be used to monitor and/or control well production of an oil and/or gas extraction system. For example, the output of the fluid classification model may be received by a flow meter and utilized by the flow meter for determination of individual phase flow rates. In some instances, the output of the models may be utilized for detection of formation water breakthrough. For example, water that was previously separated from the wellbore may enter into a producing oil and/or gas well. The output of the models may serve as detection of formation water breakthrough and may be utilized to control well production of the oil and/or gas extraction system. Injection wells may be utilized to maintain reservoir pressure and control oil and/or gas production. In some instances, water may be injected and may breakthrough into the producing well. As such, in response to detection of formation water breakthrough (e.g., fluid classification that includes water, water in liquid ratio above threshold, and so forth), operation and/or control of the injection well may be adjusted to reduce and/or eliminate formation water breakthrough. Additionally or alternatively, the output of the models may be utilized to control injection of fluids (e.g., chemicals, such as hydrate inhibitors). Gas hydrate may form during water production. The quantity of water (e.g., fluid classification, water in liquid ratio) may be utilized to determine appropriate chemical treatments and adjust chemical treatments (e.g., increase dosage, decrease dosage) based on changes in the water production. In some instances, the outputs of the model may be transmitted to a control system (e.g., computing system 900) that may utilize the outputs in monitoring and/or adjusting operation of an oil and/or gas extraction system. For example, in response to an increase in water production (e.g., increase in water in liquid ratio, fluid classification with water, or any combination thereof), the control system may adjust operation of one or more components of the oil and/or gas extraction system to increase chemical dosages and thereby inhibit gas hydrate formation. Additionally, the referenced flowcharts are given as an illustrative tool and further decision and process blocks may also be added depending on implementations.

As used herein, the terms “inner” and “outer”; “up” and “down”; “upper” and “lower”; “upward” and “downward”; “above” and “below”; “inward” and “outward”; and other like terms as used herein refer to relative positions to one another and are not intended to denote a particular direction or spatial orientation. The terms “couple,” “coupled,” “connect,” “connection,” “connected,” “in connection with,” and “connecting” refer to “in direct connection with” or “in connection with via one or more intermediate elements or members.”

The foregoing description, for purposes of explanation, has been described with reference to specific embodiments. However, the illustrative discussions above are not intended to be exhaustive or to limit the disclosure to the precise forms disclosed. Many modifications and variations are possible in view of the above teachings. Moreover, the order in which the elements of the methods described herein are illustrated and described may be re-arranged, and/or two or more elements may occur simultaneously. The embodiments were chosen and described to best explain the principles of the disclosure and its practical applications, to thereby enable others skilled in the art to best utilize the disclosure and various embodiments with various modifications as are suited to the particular use contemplated.

Finally, the techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as “means for [perform]ing [a function] . . . ” or “step for [perform]ing [a function] . . . ,” it is intended that such elements are to be interpreted under 35 U.S.C. § 112(f). However, for any claims containing elements designated in any other manner, it is intended that such elements are not to be interpreted under 35 U.S.C. § 112(f).

What is claimed is:

1. One or more non-transitory, computer-readable media comprising instructions that, when executed by processing circuitry, are configured to cause the processing circuitry to:

receive measurement data associated with a fluid, the measurement data corresponding to a microwave signal reflected from the fluid;

determine a set of fluid properties based on the measurement data;

determine fluid classification data associated with the fluid based on an analysis of the measurement data and the set of fluid properties, by determining a set of fluid classification probabilities, the determining the fluid classification data comprising:

inputting at least one of the set of fluid properties to a decision-tree model comprising a plurality of threshold decision nodes, each threshold decision node:

comparing a fluid-property value to a corresponding threshold fluid-property value; and selecting a branch of the decision-tree model based on the comparing until reaching a classification terminal node associated with the fluid classification data, the classification terminal node being associated with a set of fluid classification probabilities, the fluid classification data being generated by selecting a highest fluid classification probability associated with the classification terminal node; and at each of the plurality of threshold decision nodes:

comparing a permittivity standard deviation value to a threshold permittivity standard deviation value;

responsive to the permittivity standard deviation value falling within the threshold permittivity standard deviation value, comparing an average permittivity value to a first threshold average permittivity value to reach the classification terminal node, the classification terminal node comprising at least one of:

a dry gas terminal node corresponding to a dry gas fluid classification when the average permittivity value falls within the first threshold average permittivity value; or an oil fluid terminal node corresponding to an oil fluid classification when the average permittivity value meets or exceeds the first threshold average permittivity value; and responsive to the permittivity standard deviation value meeting or exceeding the threshold permittivity standard deviation value:

comparing a minimum permittivity value to a threshold minimum permittivity value; and comparing the average permittivity value to a second threshold average permittivity value;

generate a salinity value associated with the fluid based on an analysis of the measurement data, the set of fluid properties, and the fluid classification data, the generating the salinity value comprising generating the salinity value based on the fluid classification data associated with the classification terminal node; and transmit the salinity value to a control system of an oil and gas extraction system, the control system being configured to adjust operation of one or more components of the oil and gas extraction system based on the salinity value.

2. The one or more non-transitory, computer-readable media of claim 1, wherein the instructions, when executed by the processing circuitry, are further configured to cause the processing circuitry to:

generate an initial salinity value based on a mixing model associated with the fluid classification data; and generate the salinity value based on the analysis comprising the initial salinity value.

3. The one or more non-transitory, computer-readable media of claim 1, wherein the instructions, when executed by the processing circuitry, are further configured to cause the processing circuitry to:

receive historical data associated with one or more fluid classifications, wherein the historical data comprises historical measurement data and a historical set of fluid properties; and train a first machine learning model using a subset of the historical data associated with a first fluid classification.

4. The one or more non-transitory, computer-readable media of claim 3, wherein the instructions, when executed by the processing circuitry, are further configured to cause the processing circuitry to:

train a second machine learning model using a second subset of the historical data associated with a second fluid classification; and based on the fluid classification data indicating the fluid corresponds to the second fluid classification, perform the analysis utilizing the second machine learning model.

* * * * *